US012667541B2

(12) United States Patent
Forster et al.

(10) Patent No.: US 12,667,541 B2
(45) Date of Patent: Jun. 30, 2026

(54) DRY POWDER FORMULATION FOR PULMONARY DELIVERY AND METHODS OF USE

(71) Applicant: AstraZeneca AB, Södertälje (SE)

(72) Inventors: Laura Forster, Bad Homburg vor der Höhe (DE); Mats Hertel, Bad Homburg vor der Höhe (DE); Christoph Gremmel, Bad Homburg vor der Höhe (DE)

(73) Assignee: AstraZeneca AB, Södertälje (SE)

( * ) Notice: Subject to any disclaimer, the term of this patent is extended or adjusted under 35 U.S.C. 154(b) by 796 days.

(21) Appl. No.: 17/907,120

(22) PCT Filed: Mar. 26, 2021

(86) PCT No.: PCT/EP2021/057903
§ 371 (c)(1),
(2) Date: Sep. 23, 2022

(87) PCT Pub. No.: WO2021/191416
PCT Pub. Date: Sep. 30, 2021

(65) Prior Publication Data
US 2024/0207176 A1      Jun. 27, 2024

Related U.S. Application Data

(60) Provisional application No. 63/000,533, filed on Mar. 27, 2020.

(51) Int. Cl.
*A61K 9/00* (2006.01)
*A61K 9/14* (2006.01)
*A61K 31/506* (2006.01)
*A61K 47/26* (2006.01)

(52) U.S. Cl.
CPC ............ *A61K 9/0075* (2013.01); *A61K 9/145* (2013.01); *A61K 31/506* (2013.01); *A61K 47/26* (2013.01)

(58) Field of Classification Search
CPC .... A61K 9/0075; A61K 9/145; A61K 31/506; A61P 29/00
See application file for complete search history.

(56) References Cited

U.S. PATENT DOCUMENTS

2017/0121327 A1* 5/2017 Fatheree .............. A61K 31/437

FOREIGN PATENT DOCUMENTS

WO      2010-085684 A1      7/2010

OTHER PUBLICATIONS

Donovan et al., International Journal of Pharmaceutics 402 (2010) 1-9 (Year: 2010).*
Kinnunen et al., An Investigation into the Effect of Fine Lactose Particles on the Fluidization Behaviour and Aerosolization Performance of Carrier-Based Dry Powder Inhaler Formulations, AAPS PharmSciTech, 2014, 15:4, pp. 898-909.
(Continued)

*Primary Examiner* — San Ming R Hui

(57) ABSTRACT

Pharmaceutical compositions are provided for pulmonary administration of a JAK inhibitor, and, for example, dry powder formulations that include a JAK inhibitor and an agglomerated lactose carrier. Methods of making and using the pharmaceutical composition, as well as kits and dosage forms are also provided.

15 Claims, 4 Drawing Sheets

(56)  References Cited

OTHER PUBLICATIONS

Du, et al., Evaluation of Granulated Lactose as a Carrier for DPI Formulations 1: Effect of Granule Size, 2014, 15:6, pp. 1417-1428.
Sibum, et al., Challenges for pulmonary delivery of high powder doses, Int'l. J. of Pharm., 2018, 548:1, pp. 325-336.
Int'l. Search Report for PCT/EP2021/057903 mailed Jul. 7, 2021.

* cited by examiner

12% drug load                    24% drug load

30% drug load                    40% drug load n = 9, 3 devices, 3 doses per device, 1 actuation per dose
error bars = standard deviation n = 3, 3 devices, 1 actuation per device
error bars = standard deviation n = 3, 3 devices, 1 actuation per device
error bars = standard deviation

DRY POWDER FORMULATION FOR PULMONARY DELIVERY AND METHODS OF USE

CROSS-REFERENCE TO RELATED APPLICATIONS

This application is a U.S. National Stage application of International Application No. PCT/EP2021/057903, filed on Mar. 26, 2021, said International Application No. PCT/EP2021/057903 claims benefit under 35 U.S.C. § 119(e) of the U.S. Provisional Application No. 63/000,533, filed Mar. 27, 2020. Each of the above listed applications is incorporated by reference herein in its entirety for all purposes.

FIELD OF THE DISCLOSURE

Pharmaceutical compositions are provided herein for pulmonary administration of a JAK inhibitor, for example, dry powder formulations that include a JAK inhibitor and a lactose carrier, methods of making and using the pharmaceutical composition, as well as kits and dosage forms.

BACKGROUND OF THE DISCLOSURE

Pulmonary delivery of active pharmaceutical ingredients (APIs) is a way to target drug delivery to the lungs with lower systemic side effects and higher local concentrations and has been widely used for treatment of respiratory diseases such as asthma, bronchitis, chronic obstructive pulmonary disease (COPD), emphysema and rhinitis. In recent years, there has been increased interest in pulmonary administration for systemic delivery of a variety of other drug products for other indications.

Inhalation systems commonly used to deliver drug particles locally to the pulmonary air passages include dry powder inhalers (DPIs), metered dose inhalers (MDIs), and nebulizers. To achieve good particle deposition in the lungs, the drug particles generally have an aerodynamic diameter in the respirable size range, typically less than about 10 μm, and generally from about 1 μm to about 5 μm. The API is often micronized to obtain a particle size of less than 10 μm or less than 5 μm.

However, for particles with a diameter less than 10 μm, electrostatic forces and van der Waals forces are generally greater than the force of gravity, such that the bulk powder material is cohesive and resists flow under gravity except as large agglomerates. This can make the bulk powder difficult to handle and process, and difficult to disperse. Kinnunen et al. (2014) "An Investigation into the Effect of Fine Lactose Particles on the Fluidization Behaviour and Aerosolization Performance of Carrier-Based Dry Powder Inhaler Formulations." AAPS Pharm. Tech. Sci. 15(4):898-909.

One way to improve the bulk powder properties of drug particles is to combine the drug particles with a carrier particle of considerably larger particle size (typically from about 40 μm to about 100 μm or even higher) to improve flowability, dose accuracy and dispersibility. Generally, the drug particles and carrier form an ordered mixture in which the fine drug particles adhere to the carrier particles such that the composition takes on the bulk powder characteristics of the carrier particles. The adhesive force between the drug particles and the carrier should be strong enough to withstand segregation during blending and product storage, but weak enough to allow separation of the drug particle from the carrier surface upon aerosolization. The particle size, size distribution, morphology, surface roughness, surface area, flowability and surface energy of lactose carrier can influence performance of the resulting dry powder formulation. Du et al. (2014) "Evaluation of Granulated Lactose as a Carrier for DPI Formulations 1: Effect of Granule Size." AAPS Pharm. Sci. Tech. 15(6):1417-1428.

Generally, the carrier is deposited in the upper airways of the patient and the micronized drug is deposited in the lung for absorption. Srichana et al. (1998) "On the relationship between drug and carrier deposition from dry powder inhalers in vitro", Int. J. of Pharm. 167:13-23. The most commonly used carrier is lactose.

Pulmonary delivery of high API doses has unique challenges. Generally, at high concentrations, multiple drug layers may form on the carrier surface and drug pellets or agglomerates without a carrier nucleus may be formed, which are mechanically unstable and can negatively impact dose reproducibility. As a general matter, drug concentrations have been limited to between about 0.1 and 4% to reduce the risk of dose inconsistency. Sibum et al. (2018) "Challenges for pulmonary delivery of high powder doses." Int. J. Pharm. 548:325-336.

SUMMARY OF THE DISCLOSURE

Described herein are pharmaceutical compositions for pulmonary administration of a JAK inhibitor, and, for example a dry powder formulation that includes a JAK inhibitor and a suitable carrier material for inhalation as well as further optional excipients to control surface properties of the API or the carrier material. Additionally, methods of making and using the pharmaceutical composition are provided as well as kits, and unit dosages.

In one aspect, a pharmaceutical composition suitable for pulmonary administration is provided. In one aspect, the pharmaceutical composition includes a dry powder formulation containing a JAK inhibitor and a pharmaceutically acceptable lactose carrier. In one aspect, the lactose carrier is an agglomerated lactose carrier. In one aspect, the pharmaceutical composition includes from about 10 weight % (wt %) of a JAK inhibitor. In one aspect, the pharmaceutical composition includes from about 10 wt % to about 50% wt % of the JAK inhibitor. In one aspect, the pharmaceutical composition includes from about 10 wt % to about 40 wt % of the JAK inhibitor. In one aspect, the pharmaceutically acceptable agglomerated lactose carrier has a d50 from about 100 μm to about 350 μm and a d90 from about 250 μm to about 450 μm.

In one aspect, the JAK inhibitor includes a compound or a pharmaceutically acceptable salt of Formula I.

Formula I

In one aspect, the pharmaceutically acceptable salt includes the fumarate salt or hemi-fumarate salt of the compound of Formula I.

In one aspect, the JAK inhibitor is micronized. In one aspect, the micronized JAK inhibitor has a d90 from about 1 μm to about 10 μm. In one aspect, the micronized JAK inhibitor has a d90 of less than about 5 μm.

In one aspect, the pharmaceutical composition includes a fine particle fraction from about 10% to about 80%. In one aspect, the pharmaceutical composition includes a fine particle fraction from about 40% to about 70%.

In one aspect, the lactose carrier includes a sieved agglomerated lactose carrier. In one aspect, sieved granulated lactose carrier includes α-monohydrate lactose. In one aspect, the sieved agglomerated granulated lactose carrier has a d50 from about 130 μm to about 310 μm, or from about 170 μm to about 270 μm. In one aspect, the sieved agglomerated granulated lactose carrier has a d90 from about 290 μm to about 400 μm.

In one aspect, the lactose carrier includes a crystallized agglomerated lactose carrier. In one aspect, the crystallized agglomerated lactose carrier is not sieved.

In one aspect, the pharmaceutical composition is stable at 30° C.±2° C. at 75%±5% and at 40° C.±2° C. at 75%±5% relative humidity for at least 6 months. In one aspect, the pharmaceutical composition is stable at 25° C.±2° C. at 60%±5% at relative humidity for at least 12 months.

In one aspect, a unit dosage of the pharmaceutical composition described herein is provided. In one aspect, the unit dosage includes from about 1 mg to about 5 mg of the JAK inhibitor.

In one aspect, a dry powder inhaler is provided that includes the pharmaceutical composition as described herein for pulmonary administration. In one aspect, the dry powder inhaler includes a dry powder formulation containing a JAK inhibitor described herein. In one aspect, the dry powder inhaler provides the pharmaceutical composition in a single dose that is equivalent to at least about 1 mg of the JAK inhibitor. In one aspect, the dry powder inhaler provides the pharmaceutical composition in a single dose that is equivalent to from about 1 mg to about 10 mg of the JAK inhibitor. In one aspect, the dry powder inhaler provides the pharmaceutical composition in a single dose that is equivalent to from about 1.0 mg to about 5 mg of the JAK inhibitor.

In one aspect, the dry powder inhaler is a multi-dose dry powder inhaler.

In one aspect, inhaler is a single dose inhaler.

In one aspect, a method for treating a JAK-related disease in a subject is provided. In one aspect the method includes pulmonary administration of a therapeutically effective amount of a pharmaceutical composition that includes a dry powder formulation containing a JAK inhibitor as described herein. In one aspect, the JAK-related disease is selected from inflammation, allergies, asthma, transplant rejection, T-cell mediated autoimmune diseases, Type II inflammatory diseases, diseases of the central nervous system, pulmonary diseases, delayed Type IV hypersensitivity reactions, and ocular disorders. In one aspect, the method includes pulmonary administration of a dose equivalent to from about 1.0 to about 5.0 mg JAK inhibitor. In one aspect, the dose is administered with no more than two actuations.

In one aspect, provided herein is a use of a pharmaceutical composition that includes a dry powder formulation containing a JAK inhibitor as described herein in the treatment of a JAK-related disease. In one aspect, the JAK-related disease is selected from inflammation, allergies, asthma, transplant rejection, T-cell mediated autoimmune diseases, Type II inflammatory diseases, diseases of the central nervous system, pulmonary diseases, delayed Type IV hypersensitivity reactions, and ocular disorders.

In one aspect, a method for preparing a pharmaceutical composition for pulmonary administration is provided. In one aspect, a method is provided for preparing a pharmaceutical composition that includes a dry powder formulation that includes a carrier and a JAK inhibitor. In one aspect, the carrier includes a pharmaceutically acceptable agglomerated lactose carrier. In one aspect, the JAK inhibitor includes a compound of Formula I, or a pharmaceutically acceptable salt thereof.

Disclosed herein are methods that include low shear blending of the lactose carrier and the JAK inhibitor in one or multiple steps to obtain a homogeneous powder blend (RSD content uniformity testing <10%) containing at least about 10% JAK inhibitor by weight (wt %), based on the weight of the total amount of the lactose carrier.

For example, in one aspect, the method includes:

a. sieving a minor portion of a total amount of the lactose carrier to obtain a sieved carrier having a d50 from about 100 μm to about 350 μm, and a d90 from about 250 μm to about 450 μm;

b. low shear blending of a major portion of the total amount of the lactose carrier and the JAK inhibitor to obtain a first blend;

c. sieving the first blend to obtain a sieved blend with a d50 from about 100 μm to about 350 μm, and a d90 from about 250 μm to about 450 μm; and d. low shear blending of the sieved carrier and sieved blend to obtain a second blend including a dry powder including at least about 5% JAK inhibitor by weight (wt %), based on the weight of the total amount of the lactose carrier.

In one aspect of the method, the JAK inhibitor is micronized. In one aspect, the micronized JAK inhibitor has a d90 from about 1 μm to about 10 μm. In one aspect, the micronized JAK inhibitor has a d90 of less than about 5 μm.

In one aspect of the method, the granulated lactose carrier includes α-monohydrate lactose.

In one aspect of the method, the minor portion includes less than about 50%, 40%, 30%, 20%, 10% or 5% of the total amount of lactose carrier. In one aspect of the method, the major portion includes from about 50%, 60%, 70%, 80%, 90% or 95% of the total amount of lactose carrier.

In one aspect of the method, the sieved carrier has a d50 from about 130 μm to about 310 μm, or from about 170 μm to about 270 μm. In one aspect of the method, the sieved carrier has a d90 from about 290 μm to about 400 μm. In one aspect of the method, the sieved blend has a d50 from about 130 μm to about 310 μm, or from about 170 μm to about 270 μm. In one aspect of the method, the sieved blend has a d90 from about 290 μm to about 400 μm.

In one aspect of the method, low shear blending of the major portion of the total amount of lactose carrier includes low shear blending of an unsieved lactose carrier. In one aspect, the unsieved lactose carrier includes a α-monohydrate lactose with a d10 of about 125 μm, a d50 of about 220 μm and a d90 of about 345 μm.

In one aspect, low shear blending includes free fall blending. In one aspect, free fall blending is carried out in a mechanical tumbling mixer. In one aspect, free fall blending is carried out at a rotation speed from about 5 rpm to about 60 rpm, 16 rpm to about 45 rpm, 25 rpm to about 35 rpm, about 30 to about 35 rpm, or around 33 rpm. In one aspect, free fall blending is carried out from about 5 minutes to about 30 minutes, about 10 minutes to about 15 minutes, or about 10 minutes. In one aspect, free fall blending is carried out at rotation speeds and durations as defined by equipment dimension and available settings.

In one aspect, the second blend includes an ordered mixture in which the lactose carrier covered with from about 10% to about 40% by weight JAK inhibitor. In one aspect, the method includes conditioning the blend. In one aspect, conditioning includes open storage of the blend prior to further processing.

In one aspect, a dry powder formulation for pulmonary administration is provided. In one aspect, the dry powder formulation is prepared by a method described herein.

In one aspect, a kit is provided that includes a dry powder inhaler device and a pharmaceutical composition as described herein. In one aspect, the dry powder inhaler is a multidose dry powder inhaler. In one aspect, the multidose inhaler provides from about 1 dose to about 200 doses of the pharmaceutical composition, or from about 15 doses to about 40 doses of the pharmaceutical composition. In one aspect, the pharmaceutical composition is included in a reservoir of the dry powder inhaler. In one aspect, the kit includes one or more unit dosage(s) of the pharmaceutical composition from about 1 mg to about 5 mg JAK inhibitor. In one aspect the inhaler is a single dose inhaler. In one aspect, the kit includes instructions for administration and/or storage.

6

Figure 1:
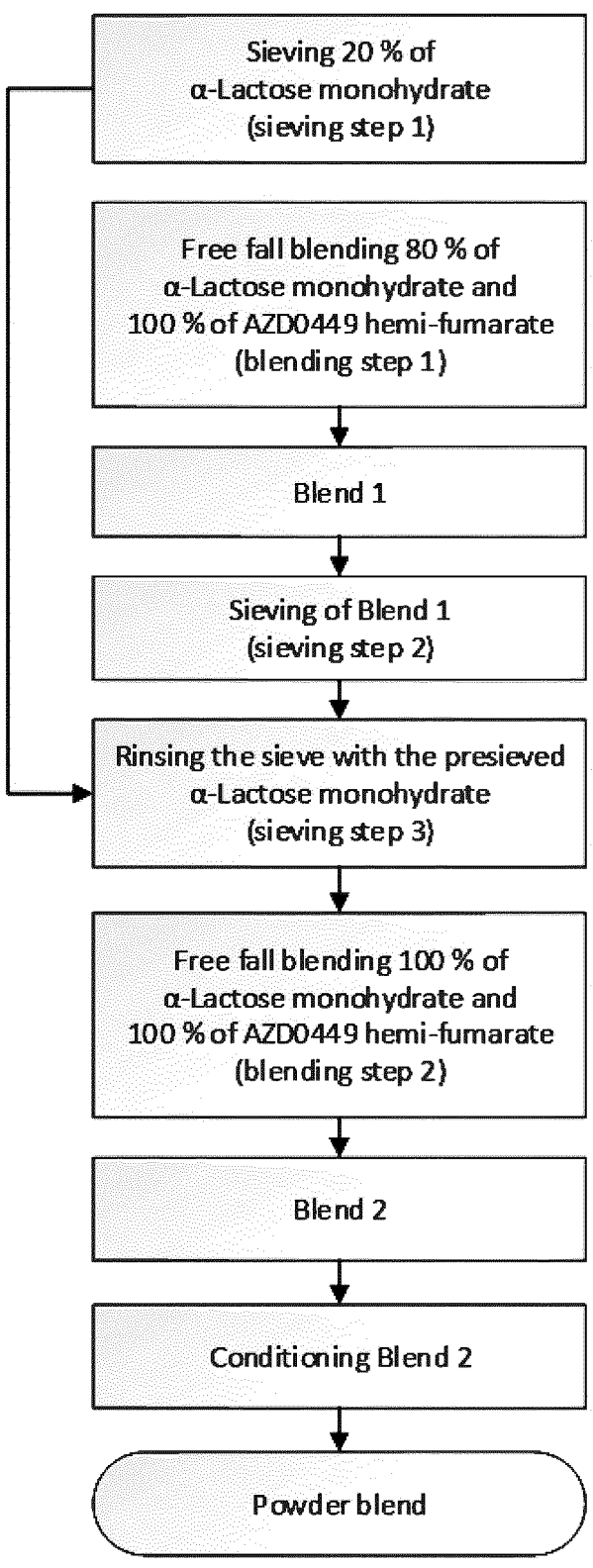
FIG. 1 is a flow chart providing an overview of a method for making a dry powder for pulmonary delivery as described herein.

(fine particle fraction (FPF)), indicating an excellent dispersion of the ordered mixture. For comparison purposes, the FPF of the pharmaceutical composition is 1.5-1.8× higher than the FPF for a commercial product in a multidose reservoir inhaler with approx. 3% drug load.

DETAILED DESCRIPTION OF THE DISCLOSURE

Described herein are pharmaceutical compositions for pulmonary administration of a JAK inhibitor, and, for example, a dry powder formulation that includes at least about 10 weight % (wt %) of a JAK inhibitor in combination with a lactose carrier. Methods of making and using the pharmaceutical composition are provided as well as kits and dosage forms.

As used herein, the term "about" is used to modify, for example, the quantity of an ingredient in a composition, concentration, volume, process temperature, process time, yield, flow rate, pressure, and ranges thereof, employed in describing the disclosure. The term "about" refers to variation in the numerical quantity that can occur, for example, through typical measuring and handling procedures used for making compounds, compositions, concentrates or formulations; through inadvertent error in these procedures; through differences in the manufacture, source, or purity of starting materials or ingredients used to carry out the methods, and other similar considerations. The term "about" also encompasses amounts that differ due to aging of a formulation with a particular initial concentration or mixture and amounts that differ due to mixing or processing a formulation with a particular initial concentration or mixture. Where modified by the term "about," the claims appended hereto include such equivalents.

"Drug load" refers to the percentage of API (herein, the JAK inhibitor) on a mass basis of the total mass of a dry powder formulation. In one aspect, the dry powder formulation includes a drug load of at least 10%, 20%, 30% by weight API. In one aspect, the dry powder formulation includes an ordered mixture in which a carrier particle is covered with API. The term "free API" refers to API in a dry powder formulation that is not adhered to a carrier particle. In one aspect, substantially all of the API in the dry powder formulation is adhered visually to the lactose carrier, for example, approximately 80%, 90% or 95% of the API is adhered to the lactose carrier. In one aspect, the drug load can be provided as the ratio of the API to the total content of the dose. In one aspect, the dry powder formulation includes an API:carrier ratio of about 10:90, 20:80, or 30:70.

In one aspect, the dry powder formulation includes an ordered mixture in which a lactose carrier is covered with a JAK inhibitor, wherein the dry powder formulation has a drug load of at least 10%, 20%, 30% by weight JAK inhibitor. In one aspect, substantially all of the JAK inhibitor in the dry powder formulation is adhered visually to the lactose carrier. In one aspect, approximately 80%, 90% or 95% of the JAK inhibitor is adhered to the lactose carrier.

In one aspect, the dry powder formulation includes an ordered mixture in which a lactose carrier is covered with a pyrimidine 2,4-diamine JAK-inhibitor, or a pharmaceutically acceptable salt thereof wherein the dry powder formulation has a drug load of at least 10%, 20%, 30% by weight pyrimidine 2,4-diamine JAK inhibitor, or pharmaceutically acceptable salt thereof. In one aspect, substantially all of the pyrimidine 2,4-diamine JAK-inhibitor, or a pharmaceutically acceptable salt thereof in the dry powder formulation is adhered visually to the lactose carrier, for example, approximately 80%, 90% or 95% of the pyrimidine 2,4-diamine JAK-inhibitor, or a pharmaceutically acceptable salt thereof in the dry powder formulation is adhered to the lactose carrier.

In one aspect, the dry powder formulation includes an ordered mixture in which a lactose carrier is covered with a JAK inhibitor according to Formula I, or a pharmaceutically acceptable salt thereof wherein the dry powder formulation has a drug load of at least 10%, 20%, 30% by weight of a compound according to Formula I, or a pharmaceutically acceptable salt thereof. In one aspect, substantially all of the JAK inhibitor according to Formula I, or a pharmaceutically acceptable salt thereof in the dry powder formulation is adhered visually to the lactose carrier, for example, approximately 80%, 90% or 95% of the JAK inhibitor according to Formula I, or a pharmaceutically acceptable salt thereof in the dry powder formulation is adhered to the lactose carrier.

In one aspect, the dry powder formulation includes an ordered mixture in which a lactose carrier is covered with a JAK inhibitor according to Formula I, or a pharmaceutically acceptable salt thereof, wherein the dry powder formulation has a drug load of at least 10%, 20%, 30% by weight of compound according to Formula I, or a pharmaceutically acceptable salt thereof. In one aspect, substantially all of the JAK inhibitor according to Formula I, or a pharmaceutically acceptable salt thereof in the dry powder formulation is adhered visually to the lactose carrier, for example, approximately 80%, 90% or 95% of the JAK inhibitor according to Formula I, or a pharmaceutically acceptable salt thereof in the dry powder formulation is adhered to the lactose carrier. In one aspect, the lactose carrier includes α-lactose monohydrate. In one aspect, the pharmaceutically acceptable salt is fumarate or hemi-fumarate.

"Metered dose" (MD) of a dry powder formulation is the total mass of JAK inhibitor metered in the dosing receptacle or reservoir or single dose unit of a dry powder inhaler. The "nominal dose" (ND) is the target dose. The MD is different from the amount of drug that is delivered to the patient which is referred to a "delivered dose" (DD) or "emitted dose" (ED). In one aspect, the DD is at least about 70%, 75%, 80%, 85%, 90% or 95% of the targeted ND.

"Delivered dose" (DD) or "emitted dose" (ED) is the total mass of API emitted from a dry powder inhaler following actuation. The DD does not include material left on the internal or external surfaces of the device, or in the metering system. The DD can be determined by collecting the total emitted mass from the device in an apparatus such as a dose uniformity sampling apparatus (DUSA).

The "fine particle dose" (FPD) is the total mass of API emitted from the device following actuation which is present in an aerodynamic particle size smaller than a defined limit, generally less than about 5 μm, 4 μm, 3 μm, 2 μm or 1 μm and can also be referred to as the "respirable fraction," i.e., the percentage of API which can reach the deep lungs in a patient. The FPD can be measured using known techniques, including, for example, using an impactor or impinger, such as a twin stage impinger (TSI), multistage impinger (MSI), Andersen Cascade Impactor (ACI) or a Next Generation Impactor (NGI).

The "fine particle fraction" (FPF) is the fine particle dose (FPD) divided by the emitted dose (ED) and is expressed as a percentage calculated as FPF (ED)=(FPD/ED)×100%.

For particle size distributions, d50 values may refer to the median particle size distribution and can be determined using known methods, for example, by laser diffraction. In another embodiment, d10 and d90 values may refer, for example, volume distribution in which 10% of the particle size distribution lies below the d10 value, and 90% of the particle size distribution lies below the d90 value, respectively. Alternatively, d10 and d90 values may refer to, for instance, numeric distribution in which 10% of the particle size distribution lies below the d10 value, and 90% of the particle size distribution lies below the d90 value, respectively.

"Pharmaceutically acceptable salt" refers to salts of a compound derived from a variety of well-known organic or inorganic counter ions and can include, but are not limited to, sodium, potassium, calcium, magnesium, ammonium, and tetraalkylammonium. Pharmaceutically acceptable salts can also be formed with inorganic acids or organic acids, including, but not limited to, as acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, tartrate, tosylate and trifluoroacetate salts. Inorganic acids from which salts can be derived include, including, but not limited to, hydrochloric acid, hydrobromic acid, sulfuric acid, nitric acid, and phosphoric acid. Organic acids from which salts can be derived include, but are not limited to, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, trifluoroacetic acid, and sulfosalicylic acid. (See, for example, S. M. Berge, et al., "Pharmaceutical Salts," J. Pharm. Sci., 1977; 66:1-19 the disclosure of which is incorporated by reference herein.)

An "effective amount", "pharmaceutically effective amount" or "therapeutically effective amount" refer to an amount of a compound sufficient to treat a specified disease or one or more of its symptoms and/or to prevent the occurrence of the disease. In one aspect, the term "effective amount" refers to an amount of a compound of Formula I, or a pharmaceutically salt thereof, that will elicit a biological or medical response in a subject, for example, the reduction or inhibition of enzyme or protein activity related to a JAK and/or amelioration of symptoms of a JAK-related disease and/or the slowing or delaying of progression of a JAK-related disease. The amount of a compound which constitutes a "therapeutically effective amount" may vary depending on factors including, but not limited to, the compound used to treat the disease and its severity, and the age of the patient to be treated. Additionally, the effect may be objective (i.e. measurable by some test or marker) or subjective (i.e. the subject gives an indication of or feels an effect). One of skill in the art is able to determine a therapeutically effective amount.

"Patient" or "subject" refers to mammals and other animals, particularly humans and the methods described herein are applicable to both human therapy and veterinary applications. In one aspect, the patient or subject is a mammal. In another aspect, the patient or subject is a human. In one aspect, the subject is suffering from a JAK-related disease.

"Treat," "treating" and "treatment" refers to the reduction or inhibition of enzyme or protein activity related to JAK and amelioration of one or more symptoms of a JAK-related disease in a subject, or the slowing or delaying of progression of a JAK-related disease in a subject. The pharmaceutical composition described herein is suitable for both the therapeutic and/or prophylactic treatment of the JAK-related diseases. "Treat," "treating" and "treatment" encompass the treatment of a disease in a mammal, for example, a human, having the disease, and includes, for example:

1. preventing the disease from occurring in a mammal, for example, when such mammal is predisposed to the disease but has not yet been diagnosed as having it;
2. inhibiting the disease, for example, arresting or slowing its development;
3. relieving the disease, for example, causing regression of the disease or a symptom thereof;
4. stabilizing the disease; or combinations thereof.

As used herein, the terms "disease," "disorder" and "condition" are used interchangeably to refer to a pathological condition in a subject. As used herein, a "JAK-related" disease refers to a disease associated with the activity of one or more members of the Janus Kinase (JAK) family of protein kinases. In one aspect, the "JAK-related" disease refers to a disease associated with the activity of one or more of JAKs: JAK1, JAK2, JAK3, TYK2 or combinations thereof. In one aspect, the "JAK-related" disease refers to a disease associated with the activity of JAK1. In one aspect, the "JAK-related" disease refers to a disease associated with the activity of JAK2. In one aspect, the "JAK-related" disease refers to a disease associated with the activity of JAK3. In one aspect, the "JAK-related" disease refers to a disease associated with the activity of TYK2. Non-limiting examples of JAK-related diseases that can be treated or prevented with the pharmaceutical composition described herein include, but are not limited to: inflammation; allergies; asthma; autoimmune diseases, including systemic autoimmune disorders, transplant rejection (e.g., kidney, heart, lung, liver, pancreas, skin; host versus graft reaction (HVGR), and graft versus host reaction (GVHR)), rheumatoid arthritis, and amyotrophic lateral sclerosis; T-cell mediated autoimmune diseases such as diabetes, multiple sclerosis, psoriasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliterans and primary pulmonary hypertension; solid, delayed Type IV hypersensitivity reactions; hematologic malignancies such as leukemia and lymphomas; and ocular disorders.

Protein kinases (PKs) regulate diverse biological processes including, but not limited to, cell growth, survival, differentiation, organ formation, morphogenesis, neovascularization, tissue repair, and regeneration. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs).

There are four known mammalian JAKs: JAK1 (Janus kinase-1), JAK2, JAK3 (also known as Janus kinase, leukocyte; JAKL; and L-JAK), and TYK2 (protein-tyrosine kinase 2). Each of the JAKs is selective for the receptors of certain cytokines, though multiple JAKs can be affected by particular cytokine or signaling pathways.

The JAK/STAT pathway, and for example all four JAKs, are believed to play a role in the pathogenesis of many diseases such as asthma, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Described herein are pharmaceutical composition for pulmonary delivery of an active pharmaceutical ingredient (API), for example, a JAK inhibitor. In one aspect, the pharmaceutical composition includes a dry powder formulation that includes a JAK inhibitor and a carrier particle. In one aspect, the dry powder formulation that includes an ordered mixture in which a carrier particle is covered with a JAK inhibitor. Methods of making and using the pharmaceutical composition are also provided, as well as kits and unit dosage forms of the pharmaceutical composition.

In one aspect, the pharmaceutical composition includes a dry powder formulation that includes a JAK inhibitor and a carrier particle. In one aspect, the dry powder formulation includes an ordered mixture in which a carrier particle is covered with an API such as a JAK inhibitor. In one aspect, the dry powder formulation includes from about 10 weight % (wt %) JAK inhibitor and a pharmaceutically acceptable carrier, such as an agglomerated lactose carrier. In one aspect, the dry powder formulation includes at least about 10 wt %, 15 wt %, 20 wt %, 25 wt % or 30 wt % JAK inhibitor and up to about 30 wt %, 40 wt % or 50 wt % JAK inhibitor. In one aspect, the dry powder formulation includes from about 10 wt % to about 50 wt %, or from about 10 wt % to about 30 wt % JAK inhibitor. In one aspect, substantially all of the JAK inhibitor in the dry powder formulation is adhered visually to the lactose carrier, for example, approximately 80%, 90% or 95% of the JAK inhibitor is adhered to the lactose carrier.

In one aspect, the dry powder formulation includes an ordered mixture in which a lactose carrier is covered with from about 10 weight % (wt %) JAK inhibitor. In one aspect, the dry powder formulation includes an ordered mixture in which a lactose carrier is covered with at least about 10 wt %, 15 wt %, 20 wt %, 25 wt % or 30 wt % JAK inhibitor and up to about 30 wt %, 40 wt % or 50 wt % JAK inhibitor. In one aspect, the dry powder formulation includes an ordered mixture in which a lactose carrier is covered with from about 10 wt % to about 50 wt %, or from about 10 wt % to about 30 wt % JAK inhibitor. In one aspect, substantially all of the JAK inhibitor in the dry powder formulation is adhered visually to the lactose carrier, for example, approximately 80%, 90% or 95% of the JAK inhibitor in the dry powder formulation is adhered to the lactose carrier. In one aspect, the dry powder formulation includes less than about 20%, 10% or 5% free JAK inhibitor.

In one aspect, the dry powder formulation includes an ordered mixture in which a lactose carrier is covered with from about 10 weight % (wt %) of a compound according to Formula I, or a pharmaceutically acceptable salt thereof. In one aspect, the dry powder formulation includes an ordered mixture in which a lactose carrier is covered with at least about 10 wt %, 15 wt %, 20 wt %, 25 wt % or 30 wt % and up to about 30 wt %, 40 wt % or 50 wt % of a compound according to Formula I, or a pharmaceutically acceptable salt thereof. In one aspect, the dry powder formulation includes an ordered mixture in which a lactose carrier is covered with from about 10 wt % to about 50 wt %, or from about 10 wt % to about 30 wt % of a compound according to Formula I, or a pharmaceutically acceptable salt thereof.

In one aspect, substantially all of the compound according to Formula I, or a pharmaceutically acceptable salt thereof in the dry powder formulation is adhered visually to the lactose carrier, for example, approximately 80%, 90% or 95% of the compound according to Formula I, or a pharmaceutically acceptable salt thereof in the dry powder formulation is adhered to the lactose carrier.

In one aspect, the dry powder formulation includes an ordered mixture in which carrier particles that include α-monohydrate lactose are covered with from about 10 weight % (wt %) of a compound according to Formula I, or a pharmaceutically acceptable salt thereof. In one aspect, the dry powder formulation includes an ordered mixture in which carrier particles that include α-monohydrate lactose carrier are covered with at least about 10 wt %, 15 wt %, 20 wt %, 25 wt % or 30 wt % and up to about 30 wt %, 40 wt % or 50 wt % of a compound according to Formula I, or a pharmaceutically acceptable salt thereof. In one aspect, the dry powder formulation includes an ordered mixture in which carrier particles that include α-monohydrate lactose are covered with from about 10 wt % to about 50 wt %, or from about 10 wt % to about 30 wt % of a compound according to Formula I, or a pharmaceutically acceptable salt thereof. In one aspect, substantially all of the compound according to Formula I, or a pharmaceutically acceptable salt thereof in the dry powder formulation is adhered visually to the lactose carrier, for example, approximately 80%, 90% or 95% of the compound according to Formula I, or a pharmaceutically acceptable salt thereof in the dry powder formulation is adhered to the lactose carrier. In one aspect, the dry powder formulation includes less than about 20%, 10% or 5% free compound according to Formula I, or a pharmaceutically acceptable salt thereof.

In one aspect, the pharmaceutical composition includes a fine particle fraction (FPF) of at least about 10%, 20%, 30%, 40%, 50% or 60% and up to about 70%, 80%, or 90%. In one aspect, the pharmaceutical composition includes an FPF from about 10% to about 80%, from about 10% to about 70%, from about 20% to about 70%, from about 30% to about 70% or from about 40% to about 70%. In one aspect, the FPF includes a JAK inhibitor. In one aspect, the FPF includes an API that inhibits the activity of one or more of the four known mammalian JAKs: JAK1, JAK2, JAK3, TYK2 or combinations thereof. In one aspect, the FPF includes an API that inhibits the activity of JAK1. In one aspect, the FPF includes an API that inhibits the activity of JAK2. In one aspect, the FPF includes an API that inhibits the activity of JAK3. In one aspect, the FPF includes an API that inhibits the activity of TYK2.

In one aspect, the pharmaceutical composition includes a fine particle fraction (FPF) that includes at least about 10%, 20%, 30%, 40%, 50% or 60% and up to about 70%, 80%, or 90% of a compound according to Formula I, or a pharmaceutically acceptable salt thereof. In one aspect, the pharmaceutical composition includes an FPF from about 10% to about 80%, from about 10% to about 70%, from about 20% to about 70%, from about 30% to about 70% or from about 40% to about 70% of a compound according to Formula I, or a pharmaceutically acceptable salt thereof.

In one aspect, the pharmaceutical composition includes a fine particle fraction (FPF) that includes at least about 10%, 20%, 30%, 40%, 50% or 60% and up to about 70%, 80%, or 90% of a compound according to Formula I, or a pharmaceutical composition includes an FPF from about 10% to about 80%, from about 10% to about 70%, from about 20% to about 70%, from about 30% to about 70% or from about 40% to about 70% of a compound according to Formula I, or a pharmaceutically acceptable salt thereof. In one aspect, the pharmaceutically acceptable salt is fumarate or hemi-fumarate.

In one aspect, the pharmaceutical composition includes at least about 0.5 mg, 1 mg, 1.1 mg, 1.2 mg, 1.3 mg, 1.4 mg, 1.5 mg, 1.6 mg, 1.7 mg, 1.8 mg, 1.9 mg, 2 mg, or 2.5 mg and up to about 5 mg, 6 mg, 7 mg, 8 mg, 9 mg, or 10 mg JAK inhibitor per unit dose. In one aspect, the pharmaceutical composition includes from about 1 mg to about 10 mg, from about 1.5 mg to about 5 mg, or about 1 mg, 1.1 mg, 1.2 mg, 1.3 mg, 1.4 mg, 1.5 mg, 1.6 mg, 1.7 mg, 1.8 mg, 1.9 mg, 2 mg or 2.5 mg JAK inhibitor per unit dose. In one aspect, the pharmaceutical composition includes about 1.4 mg, 1.6 mg, 1.8 mg or 2.0 mg JAK inhibitor per unit dose. In one aspect, the unit dose is the metered dose (MD). In one aspect, the unit dose is the delivered dose (DD). In one aspect, the unit dose is the fine particle dose (FPD).

In one aspect, the pharmaceutical composition includes at least about 0.5 mg, 1 mg, 1.1 mg, 1.2 mg, 1.3 mg, 1.4 mg, 1.5 mg, 1.6 mg, 1.7 mg, 1.8 mg, 1.9 mg, 2 mg, or 2.5 mg and up to about 5 mg, 6 mg, 7 mg, 8 mg, 9 mg, or 10 mg of a compound according to Formula I, or a pharmaceutically acceptable salt thereof per unit dose. In one aspect, the pharmaceutical composition includes from about 1 mg to about 10 mg, from about 1.5 mg to about 5 mg, or about 1 mg, 1.1 mg, 1.2 mg, 1.3 mg, 1.4 mg, 1.5 mg, 1.6 mg, 1.7 mg, 1.8 mg, 1.9 mg, 2 mg or 2.5 mg of a compound according to Formula I, or a pharmaceutically acceptable salt thereof per unit dose. In one aspect, the pharmaceutical composition includes about 1.4 mg, 1.6 mg, 1.8 mg or 2.0 mg of a compound according to Formula I, or a pharmaceutically acceptable salt thereof per unit dose. In one aspect, the unit dose is the metered dose (MD). In one aspect, the unit dose is the delivered dose (DD). In one aspect, the unit dose is the fine particle dose (FPD).

In one aspect, the pharmaceutical composition includes at least about 0.5 mg, 1 mg, 1.1 mg, 1.2 mg, 1.3 mg, 1.4 mg, 1.5 mg, 1.6 mg, 1.7 mg, 1.8 mg, 1.9 mg, 2 mg, or 2.5 mg and up to about 5 mg, 6 mg, 7 mg, 8 mg, 9 mg, or 10 mg of a compound according to Formula I, or a pharmaceutically acceptable salt thereof per unit dose. In one aspect, the pharmaceutical composition includes from about 1 mg to about 10 mg, from about 1.5 mg to about 5 mg, or about 1 mg, 1.1 mg, 1.2 mg, 1.3 mg, 1.4 mg, 1.5 mg, 1.6 mg, 1.7 mg, 1.8 mg, 1.9 mg, 2 mg or 2.5 mg of a compound according to Formula I, or a pharmaceutically acceptable salt thereof per unit dose. In one aspect, the pharmaceutical composition includes about 1.4 mg, 1.6 mg, 1.8 mg or 2.0 mg of a compound according to Formula I, or a pharmaceutically acceptable salt thereof per unit dose. In one aspect, the unit dose is the metered dose (MD). In one aspect, the unit dose is the delivered dose (DD). In one aspect, the unit dose is the fine particle dose (FPD).

In one aspect, the pharmaceutical composition is stable under long term storage conditions. As used herein, "stable" means that there is no observable change, for example, less than about 10%, 5%, 4%, 3%, 2%, 1%, or 0.5% change, in one or more physical properties of the pharmaceutical composition and drug product performance parameters, for example, as determined by Nuclear Magnetic Resonance (NMR) spectroscopy, Mass Spectrometry (MS) or Infrared Spectroscopy (IR) and determination of fine particle dose (FPD), fine particle fraction (FPF) and delivered dose (DD) after about 1 month, 2 months, 3 months, 4 months, 5 months, 6 months or 1 year. In one aspect, the pharmaceutical composition is stable under long term storage conditions, for example, when stored at 25° C.±2° C. and 60%±5% or 30° C.±2° C. and 75%±5% or 40° C.±2° C. and 75%±5% relative humidity for at least about 6 months, or at least about 9 months.

In one aspect, the active pharmaceutical ingredient (API) includes a JAK inhibitor. In one aspect, the API modulates the activity of the JAK pathway, for example, by inhibiting one or more JAKs. In one aspect, the API inhibits the activity of one or more of the four known mammalian JAKs: JAK1, JAK2, JAK3, TYK2 or combinations thereof. In one aspect, the API inhibits the activity of JAK1. In one aspect, the API inhibits the activity of JAK2. In one aspect, the API inhibits the activity of JAK3. In one aspect, the API inhibits the activity of TYK2.

In one aspect, the JAK inhibitor is a compound of Formula I, wherein the JAK inhibitor is N2-(3,4,5-trimethyl) phenyl-5-methyl-N4-(2-oxo-2,3-dihydro-1,3-benzoxazol-5-yl)-2,4-pyrimidinediamine, or a pharmaceutically acceptable salt thereof.

In one aspect, the pharmaceutically acceptable salt formed from an inorganic acid or an organic acid. In one aspect, the pharmaceutically acceptable salt is formed from an inorganic or organic acid selected from acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, tartrate, tosylate and trifluoroacetate salts. In one aspect, the pharmaceutically acceptable salt includes fumarate or hemifumarate.

In one aspect, the API in the pharmaceutical formulation is in a crystalline form. In one aspect, the API in the pharmaceutical formulation is in an amorphous form.

In one aspect, the API particles have a d90 of less than about 10 μm, 9 μm, 8 μm, 7 μm, 6 μm, or less than about 5 μm. In one aspect, the API particles have a d90 of at least about 0.1 μm, 0.2 μm, 0.3 μm, 0.4 μm, 0.5 μm, 1 μm or 2 μm. In one aspect, the API particles have a d90 from about 0.1 μm to about 10 μm, from about 0.1 μm to about 5 μm, from about 0.5 μm to about 5 am, from about 1 μm to about 5 μm, from about 2 μm to about 5 μm or from about 3 μm to about 5 μm.

In one aspect, the API is micronized to achieve a d90 of at least about 0.1 μm, 0.2 μm, 0.3 μm, 0.4 μm, 0.5 μm, 1 μm or 2 μm and less than about 10 μm, 9 μm, 8 μm, 7 μm, 6 μm or 5 μm. In one aspect, the API is micronized to achieve a d90 from about 0.1 μm to about 10 μm, from about 0.1 μm to about 5 μm, from about 0.5 μm to about 5 μm, from about 1 μm to about 5 μm, from about 2 μm to about 5 μm or from about 3 μm to about 5 μm.

The term "micronization" refers to a method in which the average particle diameter is reduced to the micrometer range or less. "Micronized" refers to particles, for example, particles of an active pharmaceutical ingredient (API), whose average diameter has been reduced to a few microns or less. Micronized particles can be prepared using known micronization methods including, but not limited to grinding; precipitation; milling, including, for example, ball milling, jet milling or media milling; high pressure homogenization; spray-drying; spray freeze-drying; supercritical fluid technologies, including, for example, rapid expansion and antisolvent technologies; templating; microfabrication; lithography; and other particle precipitation techniques. The term "micronized" includes any physical, chemical, mechanical or other process used to provide a particle with a desired size and/or shape.

In one aspect, the pharmaceutical composition includes dry powder formulation that includes the API in combination with a carrier. In one aspect, the carrier particle is formed from an inert and physiologically acceptable excipient material. In one aspect, the carrier particle is formed from one or more materials selected from sugar alcohols, polyols and crystalline sugars. In one aspect, the carrier particle is formed from a crystalline sugar, for example mannitol, trehalose, melizitose, dextrose or lactose. In one aspect, the carrier particle is formed from mannitol.

In one aspect, the carrier particle is formed from lactose. As used herein, the term "lactose" refers to a lactose-containing component, including α-lactose, β-lactose, or a combination thereof. The lactose can be in various hydration states, including for example, anhydrous, monohydrate, dehydrate, or mixtures thereof. In one aspect, the lactose carrier includes α-lactose monohydrate, β-lactose monohydrate, α-lactose anhydrous, β-lactose anhydrous, amorphous lactose or a combination thereof. In one aspect, the lactose carrier includes α-lactose monohydrate.

In one aspect, the carrier is a granulated lactose carrier. In one aspect, the carrier is an agglomerated lactose carrier. As used herein, the term "agglomerated" refers to a particle having one or more lactose particles associated together to form a single agglomerated particle. In one aspect, the agglomerated particle includes 2 or more associated lactose particle. In one aspect, the carrier is sieved. "Sieving" refers to a process in which particles are separated by size, for example, using a mesh with an aperture size selected to obtain the desired particle size. "Sieved" refers to a composition, for example, a powder that contains lactose carrier particles, that has been separated based on particle size to obtain a desired particle size distribution. "Milling" refers to a process in which the average particle size of a composition, for example, a powder that contains lactose carrier particles, is reduced by a mechanical process that breaks the particles down to particles with a desired size distribution. In one aspect, the carrier is a sieved agglomerated lactose carrier. In one aspect, the carrier is an agglomerated lactose carrier. In one aspect, the carrier includes a crystallized agglomerated lactose carrier. In one aspect, the carrier includes a crystallized agglomerated lactose carrier. In one aspect, the crystallized agglomerated lactose carrier is not sieved. In one aspect the crystallized agglomerated lactose carrier contains single crystals.

In one aspect, the carrier particles are larger than the API particles such that the API tend to adhere to the surface of the carrier particles rather than sticking to one another. In one aspect, the average diameter of the carrier particles is at least about 5×, 10×, 20×, 30×, 40× or 50× larger than the average diameter of the API particles.

In one aspect, the carrier particles are processed, for example, by micronization, sieving, milling, compression, agglomeration or spray drying. In one aspect, the carrier particles are processed by sieving. Different methods for sieving are known and include, for example, mechanical sieving, for example, using a mechanical shaker and air-depression sieving, for example, using an air jet sieving machine.

In one aspect, the lactose carrier has a d50 of at least about 100 μm, 110 μm, 120 μm, 130 μm, 140 μm, 150 μm, 160 μm, 170 μm, 180 μm, 190 μm or 200 μm and up to about 250 μm, 260 µm, 270 µm, 280 µm, 290 µm, 300 µm, 310 µm, 320 µm, 330 µm, 340 µm or 350 µm. In one aspect, the lactose carrier has a d50 from about 100 µm to about 350 µm, from about 130 µm to about 310 µm, or from about 170 µm to about 270 µm.

In one aspect, the lactose carrier has a d90 of at least about 250 µm, 260 µm, 270 µm, 280 µm, 290 µm or 300 and up to about 350 µm, 360 µm, 370 µm, 380 µm, 390 µm, 400 µm, 410 µm, 420 µm, 430 µm, 440 µm or 450 µm. In one aspect, the lactose carrier has a d90 from about 250 µm to about 450 µm, or from about 290 µm to about 400 µm.

In one aspect, the lactose carrier is a agglomerated α-monohydrate lactose carrier with a d50 of at least about 100 µm, 110 µm, 120 µm, 130 µm, 140 µm, 150 µm, 160 µm, 170 µm, 180 µm, 190 µm or 200 µm and up to about 250 µm, 260 µm, 270 µm, 280 µm, 290 µm, 300 µm, 310 µm, 320 µm, 330 µm, 340 µm or 350 µm. In one aspect, the lactose carrier is a α-monohydrate lactose carrier with a d50 from about 100 µm to about 350 µm, from about 130 µm to about 310 µm, or from about 170 µm to about 270 µm.

In one aspect, the lactose carrier is a agglomerated α-monohydrate lactose carrier with a d90 of at least about 250 µm, 260 µm, 270 µm, 280 µm, 290 µm or 300 and up to about 350 µm, 360 µm, 370 µm, 380 µm, 390 µm, 400 µm, 410 µm, 420 µm, 430 µm, 440 µm or 450 µm. In one aspect, the lactose carrier is a α-monohydrate lactose carrier with a d90 from about 250 µm to about 450 µm, or from about 290 µm to about 400 µm.

Pulmonary administration can be used for local and/or systemic delivery of an active pharmaceutical ingredient (API) to treat pulmonary and/or non-pulmonary diseases. In one aspect, the pharmaceutical composition described herein is administered through pulmonary administration. In one aspect, the pharmaceutical composition described herein is administered using a "dry powder inhaler." The term "dry powder inhaler" (DPI) refers to a device for administering a dry powder into the lungs of a subject, for example, a breath activated device. DPI can be classified by the number of doses the device can carry. In one aspect, the DPI includes a single-unit dose reservoir. In one aspect, the DPI includes a multi-unit dose reservoir. In one aspect, the DPI includes a multi-dose reservoir. A variety of DPI devices are commercially available.

In one aspect, the DPI provides the pharmaceutical composition in a single dose that is equivalent to at least about 1 mg, 1.1 mg, 1.2 mg, 1.3 mg, 1.4 mg, 1.5 mg. 1.6 mg, 1.7 mg, 1.8 mg, 1.9 mg, 2.0 mg or 2.5 mg and up to about 5 mg, 6 mg, 7 mg, 8 mg, 9 mg or 10 mg JAK inhibitor. In one aspect, the DPI provides the pharmaceutical composition in a single dose that is equivalent to from about 1 mg to about 10 mg, or from about 1.5 mg to about 5 mg JAK inhibitor.

In one aspect, the DPI provides a single does that is equivalent to at least about 1 mg, 1.1 mg, 1.2 mg, 1.3 mg, 1.4 mg, 1.5 mg. 1.6 mg, 1.7 mg, 1.8 mg, 1.9 mg, 2.0 mg or 2.5 mg mg and up to about 5 mg, 6 mg, 7 mg, 8 mg, 9 mg or 10 mg JAK inhibitor, or from about 1 mg to about 10 mg, or from about 1.5 mg to about 5 mg JAK inhibitor. In one aspect, the dose is provided in one actuation. In one aspect, the dose is provided in no more than two actuations. The term "actuation" refers to the release of API from a dry powder inhaler by a single activation. In one aspect, the dry powder inhaler is breath-actuated.

In one aspect, the DPI is a multi-dose inhaler. In one aspect, the multi-dose inhaler provides at least about 2, 3, 4, 5, 10, 15 or 20 doses and up to about 30, 40, 50, 60, 70, 80, 90 or 100 doses of the pharmaceutical composition. In one aspect, the multi-dose inhaler provides from about 1 dose to about 200 doses, or from about 15 doses to about 40 doses of the pharmaceutical composition.

In one aspect, methods of making a pharmaceutical composition are provided. In one aspect, a method is provided for making a pharmaceutical composition that includes a dry powder formulation that includes a JAK inhibitor and a carrier particle. In one aspect, a method is provided for making a pharmaceutical composition that includes a dry powder formulation with from about 10 wt %, 15 wt %, 20 wt %, 25 wt % or 30 wt % JAK inhibitor and a pharmaceutically acceptable carrier, such as a lactose carrier. In one aspect, the dry powder includes an ordered mixture in which the carrier particles are covered with JAK inhibitor. In one aspect, a method is provided for making a pharmaceutical composition that includes a dry powder formulation that includes an ordered mixture in which lactose carrier particles are covered with from about 10 wt %, 15 wt %, 20 wt %, 25 wt % or 30 wt % JAK inhibitor.

In one aspect, the JAK inhibitor particles are micronized. In one aspect, the JAK inhibitor is micronized to achieve a d90 of at least about 0.1 µm, 0.2 µm, 0.3 µm, 0.4 µm, 0.5 µm, 1 µm or 2 µm and less than about 10 µm, 9 µm, 8 µm, 7 µm, 6 µm, or 5 µm. In one aspect, the JAK inhibitor is micronized to achieve a d90 from about 0.1 µm to about 10 µm, from about 0.1 µm to about 5 µm, from about 0.5 µm to about 5 µm, from about 1 µm to about 5 µm, from about 2 µm to about 5 µm, or from about 3 µm to about 5 µm. In one aspect, the lactose carrier includes α-monohydrate lactose. In one aspect, the lactose carrier is an agglomerated lactose carrier.

An overview of one embodiment of the method is provided in FIG. 1.

In one aspect, the method includes a first sieving step (sieving step 1) in which lactose carrier is sieved to obtain a sieved carrier with a desired particle distribution. In one aspect, a minor portion of the total amount of lactose carrier used in the method is sieved in the first sieving step. In one aspect, the minor portion of lactose carrier is less than about 50%, 40%, 30%, 20% or 10% of the total amount of lactose carrier In one aspect, the lactose carrier is sieved to obtain a sieved carrier with d50 of at least about 100 µm, 110 µm, 120 µm, 130 µm, 140 µm, 150 µm, 160 µm, 170 µm, 180 µm, 190 µm or 200 µm and up to about 250 µm, 260 µm, 270 µm, 280 µm, 290 µm, 300 µm, 310 µm, 320 µm, 330 µm, 340 µm or 350 µm. In one aspect, the lactose carrier is sieved to obtain a sieved carrier with a d50 from about 100 µm to about 350 µm, about 130 µm to about 310 µm, or about 170 µm to about 270 µm. In one aspect, the lactose carrier is sieved to obtain a sieved carrier with a d90 of at least about 250 µm, 260 µm, 270 µm, 280 µm, 290 µm or 300 µm, and up to about 400 µm, 410 µm, 420 µm, 430 µm, 440 µm or 450 µm. In one aspect, the lactose carrier is sieved to obtain a sieved carrier with a d90 from about 250 µm to about 450 µm or from about 290 µm to about 400 µm.

In one aspect, the method includes a first blending step (blending step 1) in which the JAK inhibitor is combined with unsieved lactose carrier in a mechanical blender to form a first blend (blend 1). In one aspect, a major portion of the total amount of lactose carrier used in the method is combined with the JAK inhibitor to form the first blend. In one aspect, the major portion includes from about 50%, 60%, 70%, 80%, 90% or 95% of the total amount of lactose carrier used in the method. In one aspect, the unsieved lactose carrier has a d10 of about 125 µm, a d50 of about 220 µm and a d90 of about 345 µm.

A variety of mechanical blenders are known and can be used to combine the JAK inhibitor and lactose carrier. In one aspect, the JAK inhibitor and lactose carrier are combined in a low shear blender. Examples of low shear blenders include tumbling, planetary, double cone, conical screw and ribbon blenders. In one aspect, the low shear blender is a free fall blender or a tumbling blender. Examples of commercially available low shear free fall or tumbling blenders include bind blenders, V-blenders and double cone blenders. In one aspect, the JAK inhibitor and lactose carrier are blended at rotation speeds and durations as defined by equipment dimension and available settings In another aspect, the JAK inhibitor and lactose carrier are combined in a high shear blender. In one aspect, the high shear blender combines the JAK inhibitor and lactose carrier by rotation of an impeller or paddles. In one aspect, high shear blending is carried out at a rotation speed from about 100 rpm to about 1000 rpm, 300 rpm to about 700 rpm, or about 350 rpm to about 650 rpm. In one aspect, high shear blending is carried out from about 10 seconds to about 10 minutes, about 30 seconds to about 5 minutes, or about 1 minute to about 2 minutes. In one aspect, the JAK inhibitor and lactose carrier are blended at rotation speeds and durations as defined by equipment dimension and available settings.

In one aspect, low shear blending is performed by batch processing and the "total amount of lactose carrier" refers to the amount of total amount of lactose carrier included in the batch.

In one aspect, the first blend (blend 1) is sieved (sieving step 2) to obtain a sieved blend with d50 of at least about 100 μm, 110 μm, 120 μm, 130 μm, 140 μm, 150 μm, 160 μm, 170 μm, 180 μm, 190 μm or 200 μm and up to about 250 μm, 260 μm, 270 μm, 280 μm, 290 μm, 300 μm, 310 μm, 320 μm, 330 μm, 340 μm or 350 μm. In one aspect, the first blend is sieved to obtain a sieved blend with a d50 from about 100 μm to about 350 μm, about 130 μm and about 310 μm, or about 170 μm and about 270 μm. In one aspect, the first blend is sieved to obtain a sieved blend with a d90 of at least about 250 μm, 260 μm, 270 μm, 280 μm, 290 μm or 300 μm, and up to about 400 μm, 410 μm, 420 μm, 430 μm, 440 μm or 450 μm. In one aspect, the first blend is sieved to obtain a sieved blend with a d90 from about 250 μm to about 450 μm or from about 290 μm to about 400 μm.

In one aspect, the sieved lactose carrier from sieving step 1 is combined with the sieved blend from sieving step 2 (blending step 2) to form a dry powder (a second blend). In one aspect, the sieve is rinsed with the sieved lactose carrier from step 1 before the sieved lactose carrier and sieved blend are combined. In one aspect, the sieved lactose carrier and sieved blend are combined in a low shear blender, for example, a tumbling, planetary, double cone, conical screw or ribbon blenders. In one aspect, the low shear blender is a free fall blender or a tumbling blender. In one aspect, the sieved lactose carrier and the sieved blend are blended for a period of time ranging from about 5 minutes to about 30 minutes, such as at least about 10 minutes, 15 minutes, or 20 minutes, and up to about 25 minutes or 30 minutes. In some instances, the period of time is from about 25 minutes to about 35 minutes, such as about 30 minutes to about 35 minutes, or about 30 minutes, at a rotation speed ranging from about 5 rpm to about 60 rpm, for example, from about 30 rpm to about 35 rpm, or at 31 rpm, 32 rpm, 33 rpm, 34 rpm or 35 rpm. In one aspect, the sieved lactose carrier and the sieved blend are blended for 30 minutes at 33 rpm in a free fall tumbling blender.

In one aspect, the dry powder includes from about 10 wt %, 15 wt %, 20 wt %, 25 wt % or 30 wt % JAK inhibitor and less than about 90 wt %, 85 wt %, 80 wt %, 75 wt %, or 70 wt % lactose carrier. In one aspect, the dry powder includes an ordered mixture in which the lactose carrier is covered with about 10% to about 40% by weight JAK inhibitor.

It is known that dry powders can become electrostatically charged during manufacturing and storage. In one aspect, the powder blend is "conditioned" to help reduce the amount of electrostatic charge. The term "conditioning" means that the dry powder is stored in an environment in which temperature and relativity are controlled to help reduce the amount of electrostatic charge in the powder. In one aspect, the powder blend is "conditioned" to help reach a stable fine particle dose (FPD) plateau. The term "stable" means less than 10% change/difference as per FDA guideline. The term "conditioning" means that the dry powder is stored in an environment in which temperature and relativity are controlled to help to reach a stable fine particle dose (FPD) plateau.

In one aspect, the pharmaceutical composition described herein is used to inhibit activity of one or more members of the Janus Kinase (JAK) family of protein kinases. In one aspect, the pharmaceutical composition described herein is used to inhibit JAK activity and/or associated protein activity related to JAK activity and may therefore be useful in the treatment of conditions in which such inhibition is desired and/or required. In one aspect, the pharmaceutical composition described herein is used to inhibit activity of one or more of the four known mammalian JAKs: JAK1, JAK2, JAK3 or TYK2. In one aspect, the pharmaceutical composition described herein is used to inhibit the activity of JAK3.

In one aspect, the pharmaceutical composition described herein is used to treat or prevent a JAK-related disease. Non-limiting examples of JAK-related diseases that can be treated or prevented with the pharmaceutical composition described herein include, but are not limited to: inflammation; allergies; asthma; autoimmune diseases, including systemic autoimmune disorders, transplant rejection (e.g., kidney, heart, lung, liver, pancreas, skin; host versus graft reaction (HVGR), and graft versus host reaction (GVHR)), rheumatoid arthritis, and amyotrophic lateral sclerosis; T-cell mediated autoimmune diseases such as diabetes, multiple sclerosis, psoriasis, and Sjogren's syndrome; Type II inflammatory diseases such as vascular inflammation (including vasculitis, arteritis, atherosclerosis, and coronary artery disease); diseases of the central nervous system such as stroke; pulmonary diseases such as bronchitis obliterans and primary pulmonary hypertension; solid, delayed Type IV hypersensitivity reactions; hematologic malignancies such as leukemia and lymphomas; and ocular disorders.

In one aspect, the method includes pulmonary administration of the pharmaceutical composition described herein to treat one or more conditions.

In one aspect, the method includes pulmonary administration of a pharmaceutical composition that includes a JAK inhibitor according to Formula I, or a pharmaceutically acceptable salt thereof and a lactose carrier, as described herein. In one aspect, the method includes pulmonary administration of a pharmaceutical composition that includes a JAK inhibitor according to Formula I, or a pharmaceutically acceptable salt thereof and a lactose carrier, as described herein. In one aspect, the JAK inhibitor includes N2-(3,4,5-trimethyl)phenyl-5-methyl-N4-(2-oxo-2,3-dihydro-1,3-benzoxazol-5-yl)-2,4-pyrimidinediamine, or a pharmaceutically acceptable salt thereof. In one aspect, the pharmaceutically acceptable salt comprises fumarate or hemi-fumarate.

In one aspect, the method includes pulmonary administration in which from about 50%, 55%, 60%, 65% to 70% and up to about 70%, 75%, 80%, 85% or 90%, or from about 50% to about 90%, from about 60% to about 80%, from about 65% to about 75%, or about 70% of the fine particle fraction (FPF) of the pharmaceutical composition is delivered to the lung.

In one aspect, the pharmaceutical composition described herein is administered alone. In another aspect, the pharmaceutical composition described herein is administered in combination with one or more other medicaments or therapies.

In one aspect, the method is practiced prophylactically. For example, the pharmaceutical composition described herein can be administered prior to development of a disease or disorder.

In one aspect, a method is provided for inhibiting an activity of a JAK. In one aspect, the method includes pulmonary administration of a pharmaceutical composition that includes an effective amount of a JAK inhibitor as described herein in an amount effective to inhibit activity of the JAK.

In one aspect, a method is provided for treating a JAK-related disease. In one aspect, the method includes pulmonary administration of a pharmaceutical composition that includes a JAK inhibitor as described herein in an amount effective to treat or prevent the JAK-related disease. In one aspect, the JAK-related disease is host versus graft reaction (HVGR) or graft versus host disease (GVHD).

In one aspect, a method is provided for treating or preventing allograft transplant rejection, either acute or chronic, in a transplant recipient. In one aspect, the method includes pulmonary administration of a pharmaceutical composition that includes a JAK inhibitor as described herein in an amount effective to treat or prevent allograft transplant rejection.

In another aspect, a method is provided for treating a T-cell mediated autoimmune disease. In one aspect, the method includes pulmonary administration of a pharmaceutical composition that includes a JAK inhibitor as described herein in an amount effective to treat the T-cell mediated autoimmune disease. In one aspect, autoimmune disease is multiple sclerosis (MS), psoriasis, or Sjogran's syndrome.

In one aspect, a method is provided for treating a Type IV hypersensitivity reaction. In one aspect, the method includes pulmonary administration of a pharmaceutical composition that includes a JAK inhibitor as described herein in an amount effective to treat or prevent the hypersensitivity reaction.

In one aspect, a method is provided for inhibiting a signal transduction cascade in which a JAK plays a role. In one aspect, the method includes pulmonary administration of a pharmaceutical composition that includes a JAK inhibitor as described herein in an amount effective to inhibit the signaling cascade.

In one aspect, a method is provided for treating an ocular disorder. In one aspect, the method includes pulmonary administration of a pharmaceutical composition that includes a JAK inhibitor as described herein in an amount effective to treat the ocular disorder. In one aspect, the amount administered is effective to increase tear production volume as compared to untreated tear production volume, thereby ameliorating a symptom of dry eye syndrome.

In one aspect, a kit is provided. In one aspect, the kit includes a pharmaceutical composition as described herein and a container. In one aspect, the kit includes a dry powder inhaler and a pharmaceutical composition as described herein. In one aspect, the kit includes instructions for administration and/or storage.

In one aspect, a pharmaceutical composition described herein is included in a reservoir of the dry powder inhaler. In one aspect, the dry powder inhaler contains one or more-unit doses of a pharmaceutical composition as described herein. In one aspect, the kit includes a multidose dry powder inhaler that provides at least about 1, 2, 3, 4, 5, 10, 15 or 20 doses and up to about 30, 40, 50, 60, 70, 80, 90, 100 or 200 doses of a pharmaceutical composition described herein. In one aspect, the kit includes a multidose dry powder inhaler that provides from about 2 doses to about 100 doses of a pharmaceutical composition described herein, or from about 15 doses to about 40 doses of a pharmaceutical composition described herein.

In one aspect, a unit dosage of the pharmaceutical composition includes from about 1 mg to about 5 mg JAK inhibitor. In one aspect, the dry powder inhaler provides the pharmaceutical composition in a single dose that is equivalent to at least about 1 mg, 1.1 mg, 1.2 mg, 1.3 mg, 1.4 mg, 1.5 mg, 1.6 mg, 1.7 mg, 1.8 mg, 1.9 mg, 2.0 mg, or 2.5 mg and up to about 5 mg, 6 mg, 7 mg, 8 mg, 9 mg, or 10 mg, of the JAK inhibitor. In one aspect, the unit dose is the metered dose (MD). In one aspect, the unit dose is the delivered dose (DD). In one aspect, the unit dose is the fine particle dose (FPD).

All references cited herein, including patents, patent applications, papers, text books and the like, and the references cited therein, to the extent that they are not already, are hereby incorporated herein by reference in their entirety.

WORKING EXAMPLES

Example 1. Preparation of a Dry Powder

A dry powder was prepared as follows:

A JAK inhibitor (N2-(3,4,5-trimethyl)phenyl-5-methyl-N4-(2-oxo-2,3-dihydro-1,3-benzoxazol-5-yl)-2,4-pyrimidinediamine hemi-fumarate) was prepared essentially as described in Example 1 of PCT Publication No. 2010/085684 and micronized using a jet mill micronization device to obtain a particle size with a d90 of less than 5 μm.

The coarse agglomerated crystalline lactose carrier and the JAK inhibitor are blended in one or multiple steps and portions in a low shear blender at rotation speeds and durations as defined by equipment dimension and available settings to obtain a homogeneous dry powder blend (RSD <10%).

100 parts (wt %) micronized JAK inhibitor and 80 parts (wt %) of the alpha-lactose monohydrate were added to a low shear tumbling blender and tumbled for 10 to 30 minutes at 31-35 rpm to form a first blend.

The first blend was sieved to obtain a sieved blend with a d50 between approximately 170 μm-270 μm and a d90 between approximately 290 μm-400 μm.

The sieve was rinsed using 20 parts (wt %) alpha-lactose monohydrate and combined with the first blend in the low shear tumbling blender and tumbled for 10 to 30 minutes at 31-35 rpm to form a dry powder.

Figure 2:
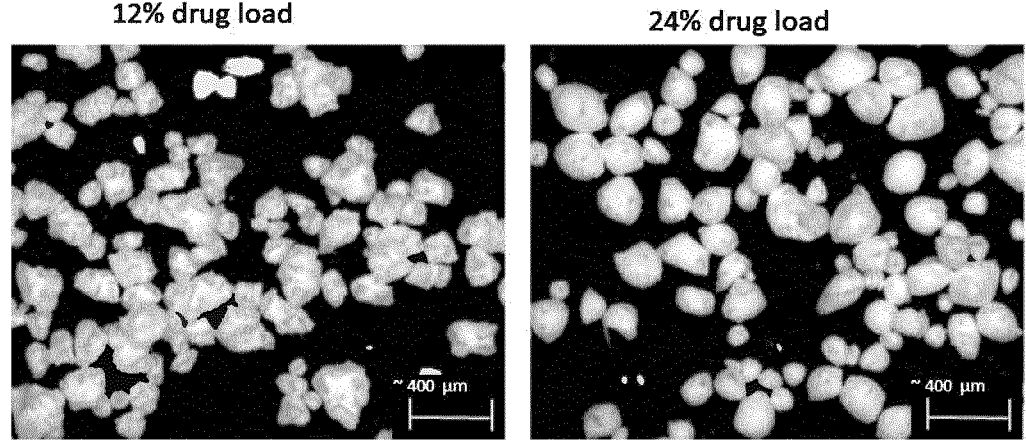
FIG. 2 illustrates light microscopy images showing particles of a pharmaceutical composition with a lactose carrier. As can be seen in the figure, there is no free active pharmaceutical ingredient (API) in the pharmaceutical composition. The API is completely collected by the lactose carrier.
Figure 2:
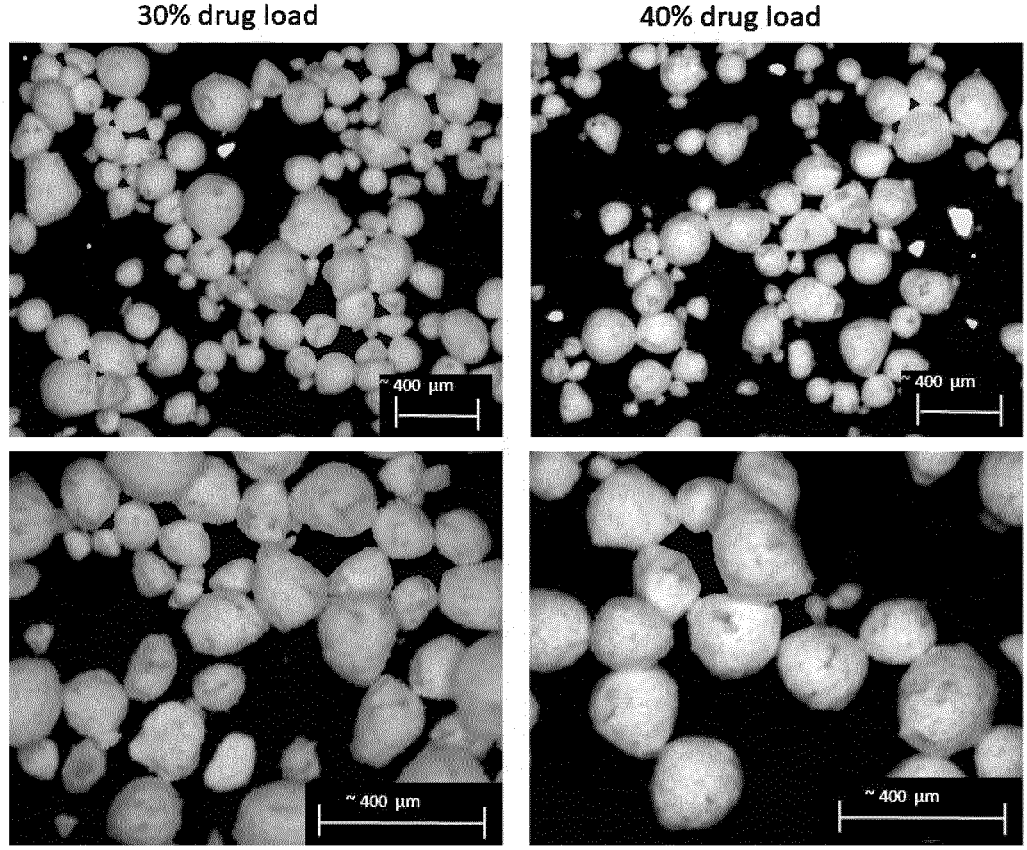

The dry powder was examined using light microscopy. As shown in FIG. 2, the JAK inhibitor was associated with the granular lactose carrier (i.e., no free JAK inhibitor was observed, i.e., no free API), resulting in a dry powder with an average 30% drug load.

Example 2. Conditioning of the Dry Powdered Blend

The dry powder prepared as described in Example 1 was conditioned at controlled temperature and humidity prior further processing under various conditions i.e., for 7-14 days at 30° C. and 75% relative humidity:

1. The dry powder was stored in volumes from 250 mL to 10 L in a glass container;
2. The dry powder was stored in a 10 L Bohle container;
3. The dry powdered blend was stored in a 10 L prototype for a Bohle container; and
4. The dry powdered blend was stored in a 20 L stainless steel lidded drum.

The obtained dry powder blend was homogeneous with regards to the API content (RSD <10%) with a stable fine particle dose and fine particle fraction over storage time at for up to 6 months.

Example 3. Delivered Dose of the Dry Powder Blend

The Delivered Dose (DD) of a single actuation of the conditioned dry powder formulation (Example 2) from a multidose reservoir inhaler was determined (9 doses from 3 different devices, 3 doses per device, 1 actuation per dose)

Figure 3:
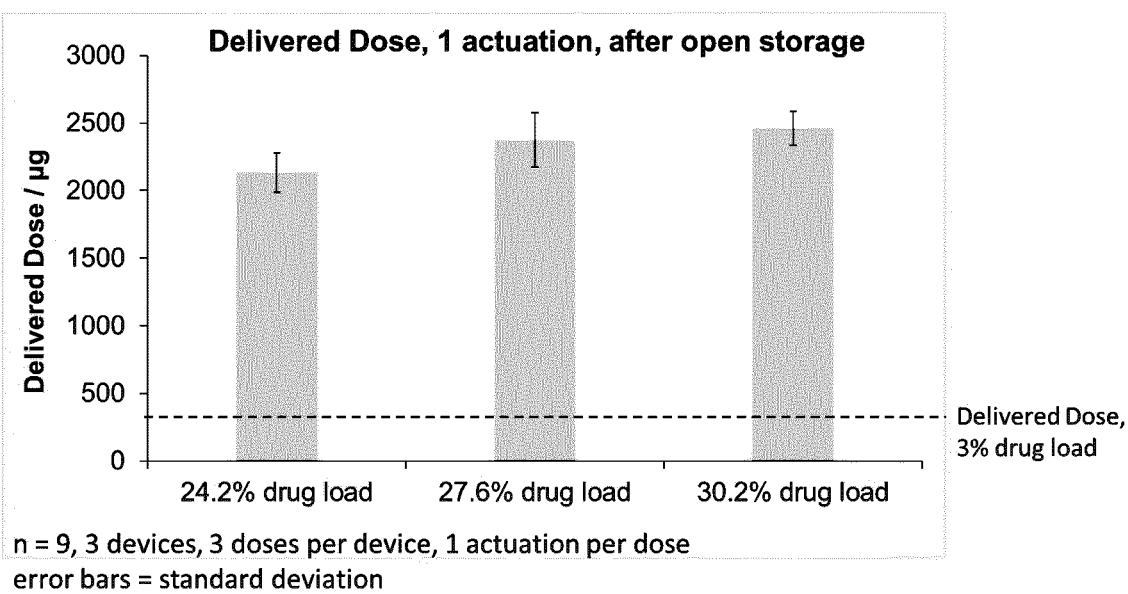
FIG. 3 is a graph showing a delivered dose (DD) of a single actuation of a pharmaceutical composition using a multidose reservoir inhaler after open storage at 30° C., 75% relative humidity, for 2 weeks (n=9, error bars indicating standard deviation). The target DD was 2.5 mg. The measured DD was approximately 2133 μg (24.2% drug load), 2374 μg (27.6% drug load) and 2459 μg (30.2% drug load), indicating that the dry powder was reproducibly dispersed into suitable aerosols for inhalation. For comparison purposes, the DD of the pharmaceutical composition is 7-8× higher than the DD for a commercial product in a multidose reservoir inhaler with approx. 3% drug load.

The target DD was 2.5 mg. As shown in FIG. 3, the measured DD was approximately 2133 µg (24.2% drug load), 2374 µg (27.6% drug load) and 2459 µg (30.2% drug load), indicating that the dry powder was reproducibly dispersed into suitable aerosols for inhalation.

For comparison purposes, the DD of the pharmaceutical composition is 7-8× higher than the DD for a commercial product in a multidose reservoir device with about 3% drug load.

Example 4. Determination of Fine Particle Fraction (>10%)

The Fine Particle Dose (FPD) for a single actuation of the conditioned dry powder formulation (Example 2) from a multidose reservoir inhaler was determined (3 devices, one actuation (dosing) per device).

Figure 4:
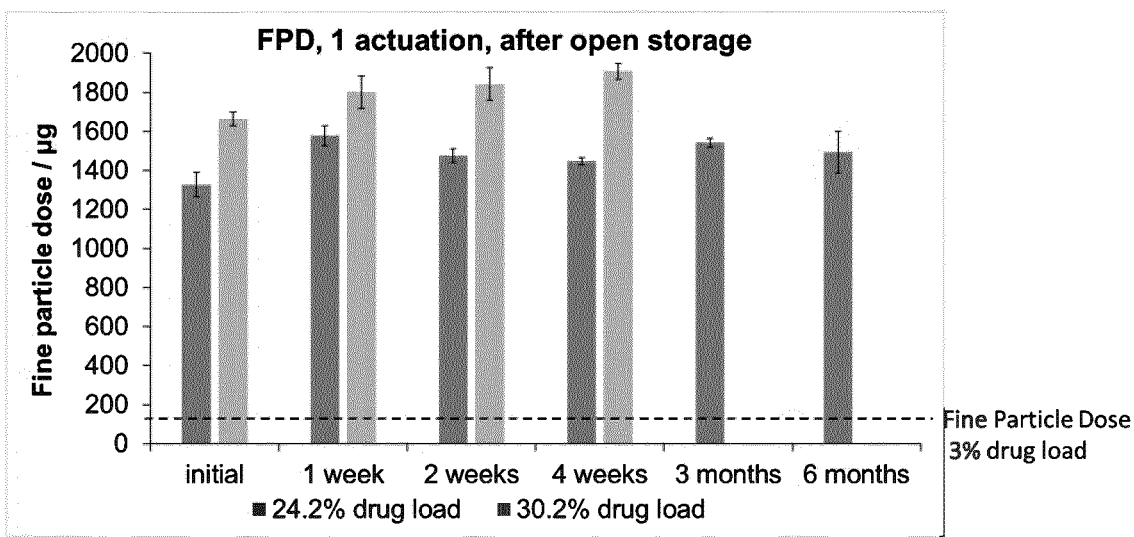
FIG. 4 is a graph showing the fine particle dose (FPD) for a single actuation of a pharmaceutical composition after open storage at 30° C., 75% relative humidity at t=0, 1 week, 2 weeks, 4 weeks, 3 months and 6 months for a composition with a 24% drug load and a composition with a 30% drug load (n=3, error bars indicating standard deviation). The target FPD (<5 μm) was 1.6 mg. The measured FPD was high and constant. For comparison purposes, the FPD of the pharmaceutical composition is 9-10× higher than the FPD for a commercial product in a multidose reservoir inhaler with approx. 3% drug load.
Figure 5:
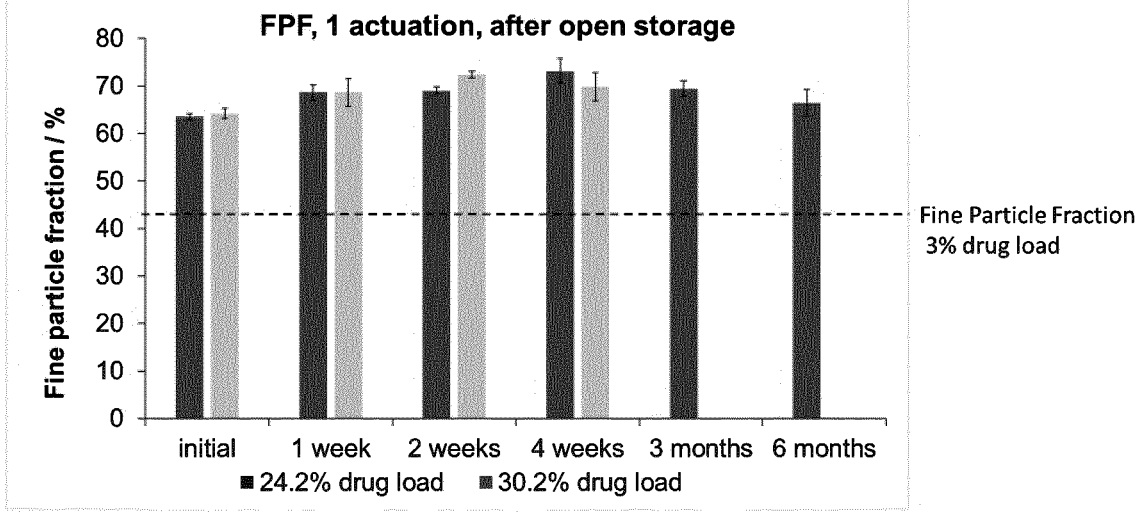
FIG. 5 is a graph showing the fine particle fraction (FPF) for a single actuation of a pharmaceutical composition after open storage at 30° C., 75% relative humidity at t=0, 1 week, 2 weeks, 4 weeks, 3 months and 6 months for a composition with a 24% drug load and a composition with a 30% drug load (n=3, error bars indicating standard deviation). About 70% of the delivered dose can be estimated to reach the lung

The target FPD (<5 µm) was 1.6 mg. As shown in FIG. 4. The measured FPD was consistently between about 1300 to 1600 (24.2% drug load) and 1600 and 1900 (30.2% drug load). About 70% of the delivered dose can be estimated to reach the lung (FPF), indicating sufficient dispersion of the ordered mixture as shown in FIG. 5.

Example 5. Stability Testing

Filled multidose reservoir inhalers were stored at at 25° C.±2° C. and 60%±5% or 30° C.±2° C. and 75%±5% for at least 9 months or 40° C.±2° C. and 75%±5% for at least 6 months. No observable degradation of API in the dry powder blend was observed as determined per Liquid Chromatography with UV-VIS detection. Fine particle dose and fine particle fraction were stable as defined per FDA guideline.

The invention claimed is:

1. A pharmaceutical composition for pulmonary administration comprising: a dry powder formulation comprising from about 10 weight % (wt %) of a JAK inhibitor or a pharmaceutically acceptable salt thereof, and a pharmaceutically acceptable agglomerated lactose carrier, the carrier having a d50 from about 100 µm to about 350 µm and a d90 from about 250 µm to about 450 µm.

2. The pharmaceutical composition according to claim 1, wherein the JAK inhibitor or a pharmaceutically acceptable salt thereof, comprises from about 10 wt % to about 50% wt % of the dry powder formulation.

3. The pharmaceutical composition according to claim 1, wherein the JAK inhibitor or a pharmaceutically acceptable salt thereof, is micronized.

4. The pharmaceutical composition according to claim 3, wherein the micronized JAK inhibitor or a pharmaceutically acceptable salt thereof, has a d90 from about 1 µm to about 10 µm.

5. The pharmaceutical composition according to claim 3, wherein the micronized JAK inhibitor or a pharmaceutically acceptable salt thereof, has a d90 of less than about 5 µm.

6. The pharmaceutical composition according to claim 1, comprising a fine particle fraction from about 10% to about 70%.

7. The pharmaceutical composition according to claim 1, comprising a sieved agglomerated lactose carrier, wherein the sieved lactose carrier comprises α-monohydrate lactose with a d50 from about 130 µm to about 310 µm, or from about 170 µm to about 270 µm.

8. The pharmaceutical composition according to claim 7, wherein the sieved lactose carrier comprises α-monohydrate lactose with a d90 from about 290 µm to about 400 µm.

9. The pharmaceutical composition according to claim 7, wherein the crystallized agglomerated lactose carrier is not sieved.

10. The pharmaceutical composition according to claim 1, wherein the pharmaceutical composition is stable at 30° C. at 75% relative humidity for at least 3 months.

11. A unit dosage of the pharmaceutical composition according to claim 1, comprising from about 1 mg to about 5 mg JAK inhibitor or a pharmaceutically acceptable salt thereof.

12. A dry powder inhaler comprising the pharmaceutical composition according to claim 1.

13. The dry powder inhaler of claim 12, wherein the dry powder inhaler comprises a multi-dose inhaler.

14. A method of treating a JAK-related disease in a subject comprising pulmonary administration of a therapeutically effective amount of a pharmaceutical composition according to claim 1.

15. The method according to claim 14, wherein the JAK-related disease is selected from inflammation, allergies, asthma, transplant rejection, T-cell mediated autoimmune diseases, Type II inflammatory diseases, diseases of the central nervous system, pulmonary diseases, delayed Type IV hypersensitivity reactions, and ocular disorders.

* * * * *